US010172654B2

(12) United States Patent
Watanabe et al.

(10) Patent No.: US 10,172,654 B2
(45) Date of Patent: Jan. 8, 2019

(54) CONTROLLING BONE COMPRESSION

(75) Inventors: Kohsuke Watanabe, Memphis, TN (US); Nathaniel Kelley Grusin, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 632 days.

(21) Appl. No.: 13/508,238

(22) PCT Filed: Nov. 10, 2010

(86) PCT No.: PCT/US2010/056254
§ 371 (c)(1),
(2), (4) Date: Jul. 6, 2012

(87) PCT Pub. No.: WO2011/060082
PCT Pub. Date: May 19, 2011

(65) Prior Publication Data

US 2012/0271309 A1 Oct. 25, 2012

Related U.S. Application Data

(60) Provisional application No. 61/259,745, filed on Nov. 10, 2009.

(51) Int. Cl.
*A61B 17/76* (2006.01)
*A61B 17/88* (2006.01)
(Continued)

(52) U.S. Cl.
CPC .......... *A61B 17/725* (2013.01); *A61B 17/744* (2013.01); *A61B 17/746* (2013.01);
(Continued)

(58) Field of Classification Search
CPC ... A61B 17/725; A61B 17/744; A61B 17/746; A61B 17/8872; A61B 17/8894;
(Continued)

(56) References Cited

U.S. PATENT DOCUMENTS 3,850,056 A * 11/1974 Allen .................... B25G 1/066 81/177.2
3,892,232 A * 7/1975 Neufeld .......................... 606/80
(Continued)

FOREIGN PATENT DOCUMENTS

JP 2004129808 A 4/2004
WO WO2005025436 A1 3/2005
(Continued)

OTHER PUBLICATIONS

Authorized officer Kang, Hee Gok, International Search Report/Written Opinion in PCT/US2010/056254 dated Jul. 27, 2011, 13 pages.

(Continued)

*Primary Examiner* — Jacqueline T Johanas
(74) *Attorney, Agent, or Firm* — Fish & Richardson P.C.

(57) ABSTRACT

Systems, devices and methods are disclosed for limiting compression of a fracture imposed by a lag screw of a fixation system that includes a fixation device, a lag screw and a compression screw. The disclosed devices, systems and methods prevent over-compression of a fracture by a lag screw caused by over rotation of the compression screw. Specifically, implementations of a lag screw driver and a compression screw driver are provided whereby an engagement between the lag screw driver and compression screw driver prevents any further lateral movement of the lag screw, thereby providing a complete stop to further advancement of the lag screw and any additional compression.

28 Claims, 9 Drawing Sheets

90
80
82
87
94
93

(51) Int. Cl.
*A61B 17/72* (2006.01)
*A61B 17/74* (2006.01)
*A61B 17/86* (2006.01)
*A61B 17/80* (2006.01)

(52) U.S. Cl.
CPC ...... *A61B 17/8685* (2013.01); *A61B 17/7225* (2013.01); *A61B 17/8061* (2013.01)

(58) Field of Classification Search
CPC . A61B 17/921; A61B 17/7225; A61B 17/742; A61B 17/7082; A61B 17/7091; A61B 17/7076; A61B 17/1725; A61B 17/8875
USPC ........ 606/64, 65, 66, 68, 96, 98, 9, 104, 99, 606/105
See application file for complete search history.

(56) References Cited

U.S. PATENT DOCUMENTS 4,716,894 A * 1/1988 Lazzeri et al. .................. 606/91
5,324,295 A * 6/1994 Shapiro ....................... 606/86 R
5,713,252 A * 2/1998 Iwinski .................. B25G 1/105 81/125.1
6,033,405 A 3/2000 Winslow et al.
6,209,428 B1 * 4/2001 Anderson ............... B25B 15/02 81/177.4
6,299,616 B1 * 10/2001 Beger ................ A61B 17/7044 606/86 A
6,379,364 B1 * 4/2002 Brace ................. A61B 17/1728 606/86 R
6,406,210 B1 * 6/2002 Parrish ...................... F16B 5/02 403/12
6,494,121 B1 * 12/2002 Hu ......................... B25B 15/02 81/438
6,712,819 B2 * 3/2004 Zucherman ........ A61B 17/7068 606/279
6,922,870 B2 * 8/2005 Tontz, Sr. ............... B25B 15/02 16/110.1
7,527,627 B2 * 5/2009 Ferrante ............... A61B 17/164 606/62
7,534,244 B2 * 5/2009 Ferrante ............... A61B 17/164 606/62
7,780,667 B2 * 8/2010 Watanabe ............ A61B 17/164 606/280
7,799,030 B2 * 9/2010 Watanabe ............ A61B 17/164 606/304
7,883,509 B2 * 2/2011 Ferrante ............... A61B 17/164 606/280
7,918,853 B2 * 4/2011 Watanabe ............ A61B 17/164 606/62
7,931,652 B2 * 4/2011 Ferrante ............... A61B 17/164 606/60
8,105,326 B2 * 1/2012 Ferrante ............... A61B 17/164 606/62
8,187,275 B2 * 5/2012 Ferrante ............... A61B 17/164 606/62
8,298,234 B2 * 10/2012 Ferrante ............... A61B 17/164 606/64
8,337,500 B2 * 12/2012 Bertagnoli ......... A61B 17/1671 606/80
8,449,544 B2 * 5/2013 Grusin ............... A61B 17/7225 606/64
8,617,161 B2 * 12/2013 Ferrante ............... A61B 17/164 606/62
8,834,469 B2 * 9/2014 Watanabe .......... A61B 17/7225 606/64
8,932,302 B2 * 1/2015 Jimenez ................ A61F 2/4611 606/105
8,939,978 B2 * 1/2015 Watanabe ............ A61B 17/164 606/62
2001/0032530 A1 * 10/2001 Han ...................... B25B 15/008 81/177.2
2002/0169453 A1 11/2002 Berger
2005/0251142 A1 11/2005 Hoffmann et al.
2006/0189997 A1 * 8/2006 Guenther et al. ............... 606/88
2007/0078460 A1 * 4/2007 Frigg et al. ..................... 606/61
2007/0168036 A1 7/2007 Ainsworth et al.
2007/0270845 A1 11/2007 Watanabe et al.
2007/0299447 A1 * 12/2007 Watanabe ............ A61B 17/164 606/71
2008/0154280 A1 * 6/2008 Schumacher ...... A61B 17/7091 606/104
2008/0255576 A1 * 10/2008 Protopsaltis .................. 606/104
2008/0262498 A1 * 10/2008 Fernandez Dell'Oca ...... 606/65
2008/0275447 A1 11/2008 Sato et al.
2008/0281326 A1 * 11/2008 Watanabe ............ A61B 17/164 606/62
2009/0088768 A1 * 4/2009 Grant ................. A61B 17/1728 606/102
2009/0088806 A1 * 4/2009 Leyden ............. A61B 17/1728 606/280
2009/0112209 A1 * 4/2009 Parrott et al. ................... 606/62
2009/0182345 A1 7/2009 Medoff et al.
2009/0209961 A1 8/2009 Ferrante et al.
2009/0216238 A1 * 8/2009 Stark .............................. 606/96
2009/0248025 A1 * 10/2009 Haidukewych et al. ....... 606/67
2010/0331843 A1 * 12/2010 Grusin ............... A61B 17/7225 606/64
2011/0060337 A1 * 3/2011 Ferrante ............... A61B 17/164 606/64
2011/0087228 A1 * 4/2011 Ferrante ............... A61B 17/164 606/64
2011/0160861 A1 * 6/2011 Jimenez ............. F16H 25/2056 623/17.16
2011/0238121 A1 * 9/2011 Watanabe ............ A61B 17/164 606/289
2012/0143192 A1 * 6/2012 Watanabe .......... A61B 17/7225 606/64
2012/0271309 A1 * 10/2012 Watanabe ............ A61B 17/725 606/64
2012/0323329 A1 * 12/2012 Jimenez ............. F16H 25/2056 623/17.16
2015/0313717 A1 * 11/2015 Lee .................... A61B 17/1604 623/17.11

FOREIGN PATENT DOCUMENTS

WO WO2005025437 A1 3/2005
WO WO2007109302 A1 9/2007
WO WO2007109302 A2 9/2007

OTHER PUBLICATIONS

Partial Supplementary European Search Report for European Application 10830668.9, dated Mar. 12, 2015.
Patent Examination Report No. 1 for Australian Application 2010319537, dated Jan. 19, 2015.
Office Action for Chinese Application No. 201080061093.9, dated Jan. 15, 2015.
Notice of Reasons for Rejection in Japanese Application No. 2017-177613 dated Jul. 2, 2018.
Notice of Reasons for Refusal issued in Japanese Application No. 2012-538953, dated Jul. 30, 2014.
Patent Examination Report No. 3 for Australian Application No. 2010319537, dated Jan. 19, 2016.
Patent Examination Report No. 2 for Australian Application No. 2010319537, dated Nov. 17, 2015.
Extended European Search Report for European Application 10830668.9, dated Sep. 11, 2015.
Communication Pursuant to Article 94(3) EPC for European Application No. 10830668.9, dated Oct. 25, 2016.
Communication Pursuant to Article 94(3) EPC for European Application No. 10830668.9, dated Nov. 2, 2017.

* cited by examiner 36
33
37
32
69
76
68a 36
71
69
72
73
74
37

76
68a

CONTROLLING BONE COMPRESSION

CROSS-REFERENCE TO RELATED APPLICATION

This application is a national stage application of PCT/US2010/056254, filed Nov. 10, 2010, and titled "CONTROLLING BONE COMPRESSION," which claims priority to and the full benefit of U.S. Provisional Application No. 61/259,745, filed Nov. 10, 2009, and titled "TOOL FOR CONTROLLING LAG SCREW COMPRESSION," the entire contents of which are incorporated herein by reference.

TECHNICAL FIELD

This disclosure relates to controlling bone compression.

BACKGROUND

A variety of devices are used to treat fractures of long bones, many of which are disclosed in co-pending and commonly-assigned U.S. patent application Ser. No. 12/074,320, which is incorporated herein by reference. Referring to FIG. 1, one such stabilizing assembly 30 includes an intramedullary nail 31 (in this case a humeral nail), a lag screw 32 and a compression screw 33. As illustrated in FIG. 1, the compression screw 33 includes an enlarged head section 34 that, in this embodiment, bears against the humerus 35 to compress the humerus 35. A threaded section 36 of the compression screw 33 passes through the nail 31 and engages a rack 35 disposed on a side of the lag screw 32 (the rack 35 is more clearly seen in FIG. 8). In some implementations, the lag screw 32 can include a threaded portion that engages the threaded section 36 of the compression screw 33. Rotating the compression screw 33 applies an axial force to the lag screw 32, which has previously been anchored in a fragment of the humerus 35 by a threaded distal end 37. Accordingly, rotating the compression screw 33 draws the lag screw 32, and the bone fragment affixed to the end 37 of the lag screw 32, in a direction along the length of the compression screw 33 and into position for proper healing.

In another example illustrated in FIG. 2, a stabilizing assembly 40 coupled to a femur 41 includes a compression plate 42, the compression screw 33 and the lag screw 32. A head section 44 of the compression plate 42 extends into the femur 41 and supports the compression screw 33 and the lag screw 32. As described above, the compression screw 33 bears against a surface of the compression plate 42 such that rotation of the compression screw 33 applies an axial force to the lag screw 32 to draw the lag screw 32 and a bone fragment in a direction along the length of the compression screw 33.

FIG. 3 illustrates another stabilizing assembly 50 applied to a proximal tibia 51. The assembly 50 includes a periarticular plate 52, the lag screw 32 and the compression screw 33. Again, the head section 34 of the compression screw 33 bears against the plate 52 to limit further insertion of the compression screw and to provide a positive stop such that rotation of the compression screw 33 interacts with the lag screw 32 causing compression of the tibia 51.

In contrast to compression plate 42 of FIG. 2, FIGS. 4-6 illustrate a stabilizing assembly 60 which includes an antegrade femoral intramedullary nail 61, the lag screw 32 and the compression screw 33 to stabilize a fracture 63 across a femoral neck 64. The designs of the nails 31, 61, plates 42, 52, and screws 32, 33 may vary greatly and may be configured to be applicable to other parts of the anatomy not specifically illustrated here or specifically addressed in this disclosure. Regardless of the designs, the compression screw 33 interacts with the lag screw 32 to compress the bone. Alternatively, the fracture can be distracted by interaction of the compression screw 33 and the lag screw 32. Additionally, the lag screw 32 and the compression screw 32 are configured to slide as a unit within the nail or plate.

However, problems may result if bone adjacent to a fracture is weak and/or prone to damage when exposed to compression, or excessive compression, force. For example, excessive compression force could cause the femoral head 65 shown in FIG. 4 to migrate towards or into the fracture site 63 resulting in misalignment. In extreme cases, excessive compression may cause the femoral head 65 to be compressed all the way into the trochanteric region 66 of the femur 41.

Further, compressing a bone more than a recommended or intended amount may cause the lag and compression screws 32, 33 to splay apart from each other, which can inhibit or prevent the screws from sliding within the intramedullary nail 31, 61 or plate 42, 52. Thus, while applying compression force using a compression screw/lag screw system 32, 33 is an important orthopaedic technique, excessive compression can be problematic and should be avoided.

Currently, separate compression screw and lag screw drivers are utilized. To limit the compressive force transmitted to the lag screw 32, some compression screw drivers are equipped with a line indicating 0 mm and/or red line indicating to the surgeon or other use that rotation of the compression screw to apply compression force should be stopped. However, even with this type of visual aid, experienced surgeons may still apply excessive compression force across a fracture site. Hence, a more reliable system, that is less prone to operator error, and that controls bone and/or fracture compression, is needed.

SUMMARY

Systems and assemblies are provided for limiting compression imposed by a compression screw on a lag screw of an orthopedic implant assembly. In one disclosed system, a lag screw driver is provided that includes a distal end for engaging the lag screw and a proximal end that includes a stop member or a stop in its structure. Hereinafter, this stop member or stop portion will be referred to simply as a "stop." The system also includes a compression screw driver that comprises a distal end for engaging the compression screw and a proximal end. The compression screw driver comprises a radially outwardly extending member disposed between the proximal and distal ends thereof that engages the stop of the lag screw driver thereby preventing any further rotation of the compression screw driver or the compression screw.

In some implementations, the system can include one or more of the following features. For example, the proximal end of the lag screw driver comprises a handle and the stop is disposed on the handle. The lag screw driver comprises an elongated cylindrical body extending between the proximal and distal ends of the lag screw driver and the elongated cylindrical body of the lag screw driver provides the stop. The lag screw driver comprises a retaining rod disposed within the elongated cylindrical body. The retaining rod comprises a proximal end that extends outward from the proximal end of the cylindrical body and serves as the stop for engaging the outwardly extending member of the compression screw driver. The retaining rod further comprises a threaded distal end for engaging interior threads disposed at the proximal end of the lag screw. The compression screw driver includes an elongated cylindrical body extending between the proximal and distal ends of the compression screw driver. The compression screw driver further comprises a retaining rod disposed within the elongated cylindrical body and the retaining rod of the compression screw driver includes a threaded distal end that threadably engages internal threads disposed at the proximal end of the compression screw.

A system for limiting compression imposed by an orthopedic implant assembly is also disclosed. In one disclosed system, a lag screw and a compression screw are provided. The lag screw comprises a threaded distal end, a proximal end and an elongated body extending therebetween. The elongated body includes a middle rack. The middle rack has a predetermined axial length and the middle rack does not extend to either the distal or proximal ends of the lag screw. In other words, there are gaps between the middle rack and the distal and proximal ends of the lag screw. The distal end of the lag screw is threaded or includes an auger-type helical end for anchoring the lag screw into bone. The system also includes a compression screw that comprises a distal end, a proximal end and an elongated body extending therebetween. The elongated body of the compression screw includes a first threaded portion and a second unthreaded portion. The first threaded portion is disposed between the distal end of the compression screw and the second unthreaded portion. The second unthreaded portion is disposed between the proximal end of the compression screw and the first threaded portion. When the compression screw is located adjacent the lag screw so that the threads of the first portion of the compression screw are enmeshed with the middle rack of the lag screw, rotation of the compression screw results in axial movement of the lag screw until the middle rack reaches the second unthreaded portion of the compression screw (or the end of the threads of the first portion). At this point, continued rotation of the compression screw results in no additional axial movement of the lag screw as the middle rack has reached the end of the first threaded portion (or the middle rack has reached the second unthreaded portion of the compression screw). When the middle rack of the lag screw reaches the end of the first threaded portion of the compression screw, this action serves as a definitive stop and further axial movement of the lag screw is prevented.

In some implementations, the system can include one or more of the following features. For example, the middle rack is disposed within a trough disposed along the elongated body of the lag screw. The trough configuration enables the side-by-side placement of the lag and compression screws to consume less cross-sectional space.

An improved fracture stabilization assembly is also provided which includes a stabilization assembly that comprises a stabilization device selected from the group consisting of a compression plate or an intramedullary nail. The stabilization device comprises a shaped opening to accommodate a compression screw and a lag screw in a side-by-side fashion. A lag screw driver and a compression screw driver are provided as described above. Operation of the lag screw driver and compression screw driver in the manner described above provides a positive stop to prevent any over-compression of the fractured bone by excessive axial movement of the lag screw caused by over rotation of the compression screw.

Similarly, a fracture stabilization assembly may include a stabilization device as described above in combination with the lag and compression screw combination described above. The lag screw includes a middle rack of a predetermined length and the compression screw includes a first portion that is threaded and a second portion that is unthreaded. When the compression screw is rotated to the extent whereby the middle rack of the lag screw reaches the second unthreaded portion of the compression screw, movement of the lag screw is positively stopped regardless of whether the compression screw continues to be rotated and over-compression of the fractured bone is avoided.

Methods for stabilizing a fracture in a bone are also disclosed. One disclosed method includes installing a stabilization device such as a compression plate or an intramedullary nail as described above. The stabilization device may have a shaped opening to accommodate a compression screw and a lag screw in a side-by-side fashion as described above. The method includes providing a lag screw, a compression screw, a lag screw driver and a compression screw driver as described above. The method includes installing the stabilization device, inserting the lag screw through the shaped opening, rotating the lag screw with the lag screw driver and anchoring the lag screw in bone disposed on the distal side of the fracture site with the threaded distal end of the lag screw. The method further includes rotating the lag screw so that the middle rack faces the portion of the shaped opening that receives the compression screw. The method further includes inserting the compression screw through the shaped opening and engaging the threads of the compression screw with the middle rack of the lag screw. The method further includes rotating the compression screw with the compression screw driver until the radially outwardly extending member of the compression screw driver engages the stop of the lag screw driver.

In some implementations, a lag screw with a middle rack as described above and a compression screw with the first threaded portion and second unthreaded portion as described above may be utilized. After the lag screw is anchored to bone disposed on a distal side of the fracture site, the compression screw is rotated until the middle rack of the lag screw reaches the second unthreaded portion of the compression screw to achieve a positive stop situation thereby avoiding over-compression of the fractured bone.

In one general aspect, a system for the limiting compression force applied by an orthopaedic fastening assembly includes a first component driver comprising a distal end for engaging a first member of the fastening assembly and a proximal end including a stop, and a second component driver comprising a distal end for engaging a second member of the fastening assembly and a proximal end, the second component driver including a structure disposed between the proximal end and the distal end of the second member that engages the stop of the first component driver to limit axial translation of the first member relative to the second member.

Implementations can include one or more of the following features. For example, the proximal end of the first component driver comprises a handle, and the stop is included on the handle. The first component driver further comprises an elongated cylindrical body extending between the proximal end and the distal end of the first component driver, and a retaining rod disposed within the elongated cylindrical body, the retaining rod comprising a proximal end that extends outward from the cylindrical body and serves as the stop. The retaining rod further comprises a threaded distal end for engaging the first member. The structure extends radially outwardly between the proximal end and the distal end of the second component driver. The structure includes a flange disposed between the proximal end and the distal end of the second component driver. The second component driver includes an elongated cylindrical body extending between the proximal end and the distal end of the second component driver, the second component driver further comprising a retaining rod disposed within the elongated cylindrical body and including a threaded distal end that threadably engages the second member.

In another general aspect, a system for the limiting compression imposed by an orthopedic implant assembly includes a first fastener assembly member comprising a threaded distal end, a proximal end, and an elongated body extending therebetween, the elongated body of the first fastener assembly member having a cooperation structure having a predetermined axial length and not extending to the distal end or the proximal end of the first fastener assembly member, and a second fastener assembly member comprising a distal end, a proximal end, and an elongated body extending therebetween, the elongated body of the second fastener assembly member having a first portion and a second portion, the first portion being disposed between the proximal end and the distal end of the second fastener assembly member, and the second portion being disposed between the proximal end of the second fastener assembly member and the first portion, the first portion having a complimentary cooperation structure configured to engage the cooperation structure of the first fastener assembly member, and the second portion being configured to not engage the cooperation structure of the first fastener assembly member. When second fastener assembly member is located adjacent to the first fastener assembly member so that the complimentary cooperation structure of the first portion of the second fastener assembly member is engaged with the cooperation structure of the first fastener assembly member, adjustment of the second fastener assembly member results in axial movement of the first fastener assembly member relative to the second fastener assembly member until the cooperation structure of the first fastener assembly member reaches the second portion of the second fastener assembly member.

Implementations can include one or more of the following features. For example, portions of the elongated body of the first fastener assembly member disposed between the cooperation structure of the first fastener assembly member and the proximal end of the first fastener assembly member and the distal end of the first fastener assembly member are configured to not engage the complimentary cooperation structure of the second fastener assembly member. The cooperation structure of the first fastener assembly member is disposed within a trough of the elongated body of the first fastener assembly member.

In another general aspect, an orthopaedic device includes a stabilization structure selected from the group consisting of a plate and an intramedullary nail, the stabilization structure comprising a shaped opening configured to receive a first member and a second member in a side-by-side arrangement, a first driver having a distal end for engaging the first member and a proximal end having a stop surface, and a second driver having a distal end for engaging the second member and a proximal end, the second driver having a radially outwardly extending portion disposed between the proximal and distal ends thereof, the radially outwardly extending portion being configured to engage the stop surface of the first driver during use to limit relative movement between the first driver and the second driver.

Implementations can include one or more of the following features. For example, the proximal end of the first driver comprises a handle, and the stop is located on the handle. The first driver further comprises an elongated cylindrical body extending between the proximal and distal ends thereof, the first driver further comprising a retaining rod disposed within the elongated cylindrical body, the retaining rod comprising a proximal end that extends outward from the cylindrical body and serves as the stop. The first driver further comprises an elongated cylindrical body extending between the proximal and distal ends thereof, the proximal end of the cylindrical body being connected to a handle, the first driver further comprising a retaining rod disposed within the elongated cylindrical body, the retaining rod comprising a proximal end that extends outward from the cylindrical body, at least one of the proximal end of the retaining rod, the handle, or the cylindrical body serving as the stop. The retaining rod of the first driver further comprises a threaded distal end for engaging the first member. The distal end of the retaining rod of the first driver is threaded for threadably engaging the first member. The distal end of the first driver is forked for engaging and rotating the first member. The distal end of the first driver comprises an element for rotating the first member that is selected from the group consisting of a female polygonal wrench socket, a male polygonal wrench, a transverse driver blade, an Allen-type driver element, a Phillips-type driver element, and a pair of prong members.

In another general aspect, an orthopaedic device includes a stabilization structure selected from the group consisting of a plate and an intramedullary nail, the stabilization structure having a shaped opening configured to receive a first member and a second member in a side-by-side arrangement, the first member comprising a threaded distal end, a proximal end, and an elongated body extending therebetween that includes a cooperation structure, the cooperation structure having a predetermined axial length and not extending to either the distal or proximal ends of the first member, and the second member comprising a distal end, a proximal end, and an elongated body extending therebetween that includes a first portion and a second portion, the first portion being disposed between the proximal end and the distal end of the second member and the second portion being disposed between the proximal end of the second member and the first portion, the first portion having threads for engagement with the cooperation structure of the first member and the second portion being unthreaded. When the second member is located adjacent to the first member so that the threads of the first portion of the second member engage the cooperation structure of the first member, rotation of the second member results in axial movement of the first member relative to the second member until the cooperation structure reaches the second portion of the second member.

Implementations can include one or more of the following features. For example, portions of the elongated body of the first member disposed between the cooperation structure and the proximal end of the first member and the threaded distal end of the first member are configured to not engage the threads of the second member. The cooperation structure is disposed within a trough of the elongated body of the first member.

In another general aspect, a method for stabilizing a bone includes installing a stabilization structure selected from the group consisting of a plate and an intramedullary nail, the stabilization structure comprising a shaped opening configured to receive a first member and a second member in a side-by-side arrangement, providing the first member, the second member, a first driver, and a second driver, the first member comprising a threaded distal end, a proximal end for engagement with a first driver and a cooperation structure for engaging the second member, the first driver comprising a distal end for engaging the first member and a proximal end comprising stop, the second driver comprising a distal end for engaging the second member and a proximal end, the second driver comprising a radially outwardly extending member disposed between the proximal and distal ends thereof for engaging the stop of the first driver, inserting the first member through the shaped opening and engaging bone with the threaded distal end of the first member by rotating the first member with the first driver, inserting the second member through the shaped opening alongside the first member such that threads of the second member engage the cooperation structure of the first member, and rotating the second member with the second driver until the radially outwardly extending member of the second driver engages the stop of the first driver.

Other advantages and features will be apparent from the following detailed description when read in conjunction with the attached drawings.

It should be understood that the drawings are not necessarily to scale and that the figures are sometimes illustrated diagrammatically and in partial views. In certain instances, details which are not necessary for an understanding of the disclosure or which render other details difficult to perceive may have been omitted. It should be understood that this disclosure is not limited to the particular implementations illustrated herein.

DETAILED DESCRIPTION

Figures 7, 8:
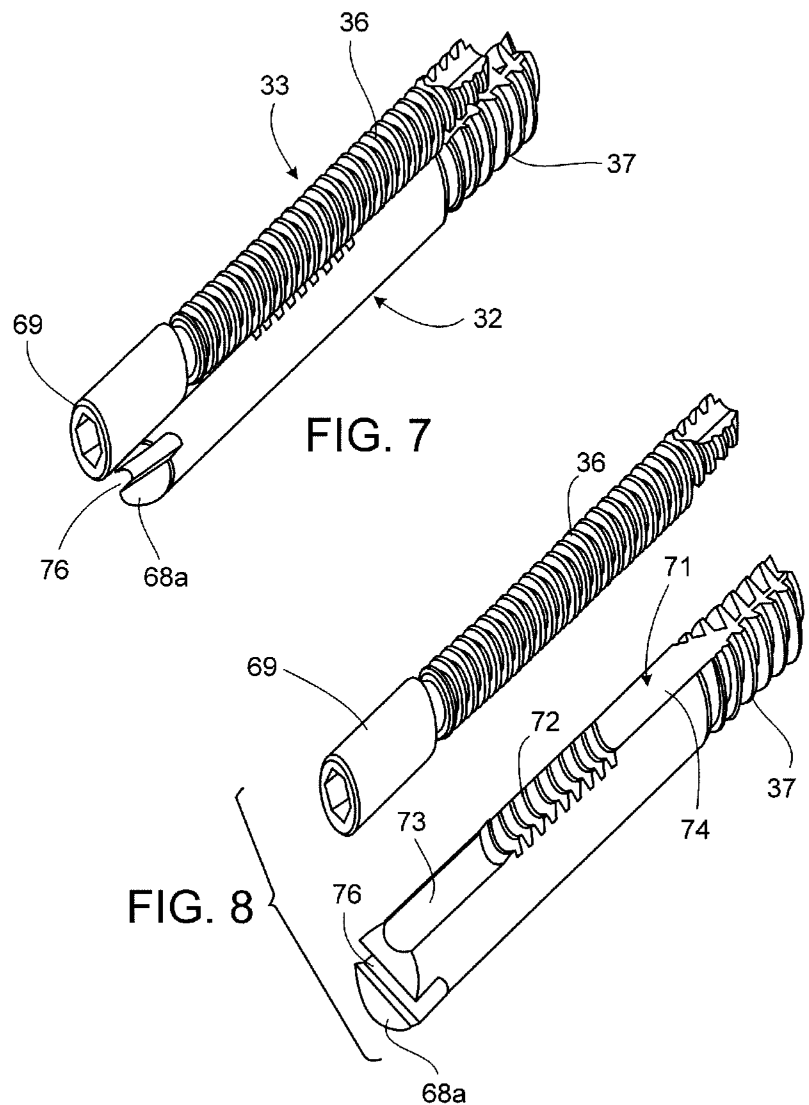
FIG. 7 is a perspective view of a fastening assembly.
FIG. 8 is an exploded view of the fastening assembly of FIG. 7.
Figure 9:
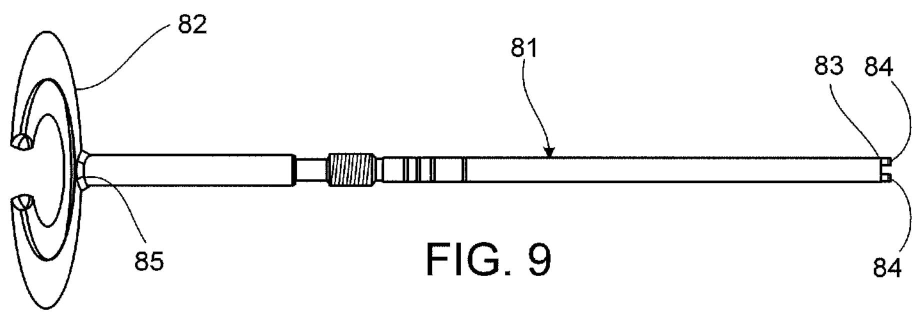
FIG. 9 is a side view of a driver tool for driving a fastener.
Figure 10:
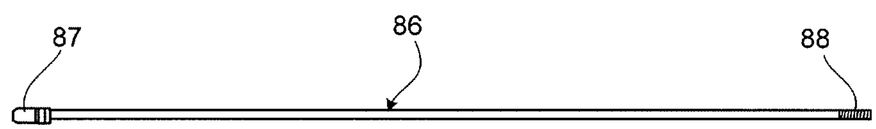
FIG. 10 is a side view of a retaining rod for use with the tool of FIG. 9.
Figure 11:
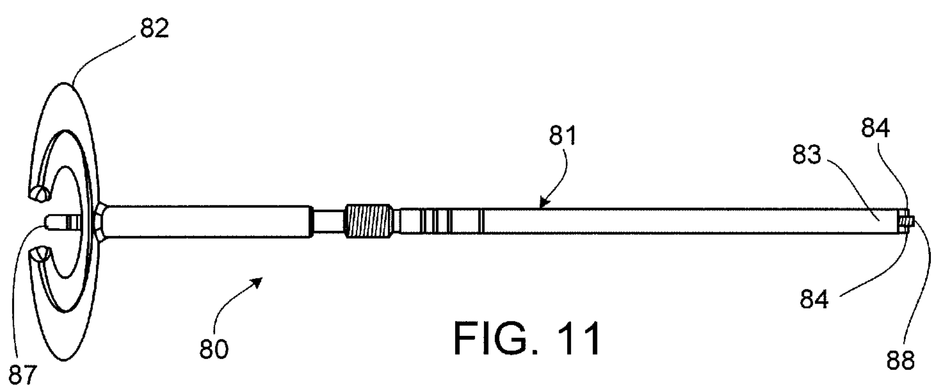
FIG. 11 is a side view of the tool of FIG. 9 with the retaining rod of FIG. 10.
Figure 12:
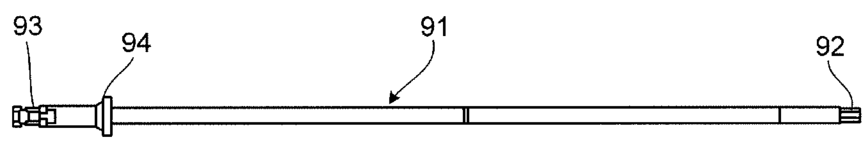
FIG. 12 is a side view of another tool for driving a fastener.
Figure 13:
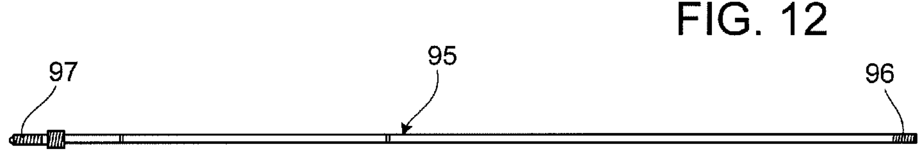
FIG. 13 is a side view of another retaining rod for use with the tool of FIG. 12.
Figure 14:
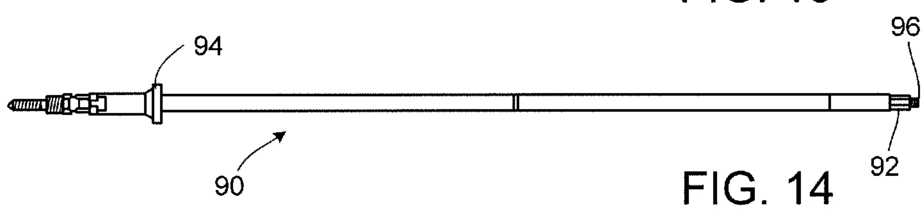
FIG. 14 is a side view of the retaining rod of FIG. 13 with the tool of FIG. 12.

Referring to FIGS. 7 and 8, the lag screw 32 includes the threaded distal end 37 that engages or anchors the lag screw 32 into a bone. The compression screw 33 includes a threaded section 36. A proximal end 68 of the lag screw is configured to engage a lag screw driver 80 (FIGS. 9-11). Similarly, the compression screw 33 includes a proximal end 69 for engagement with a compression screw driver 90 (FIGS. 12-14).

Figure 1:
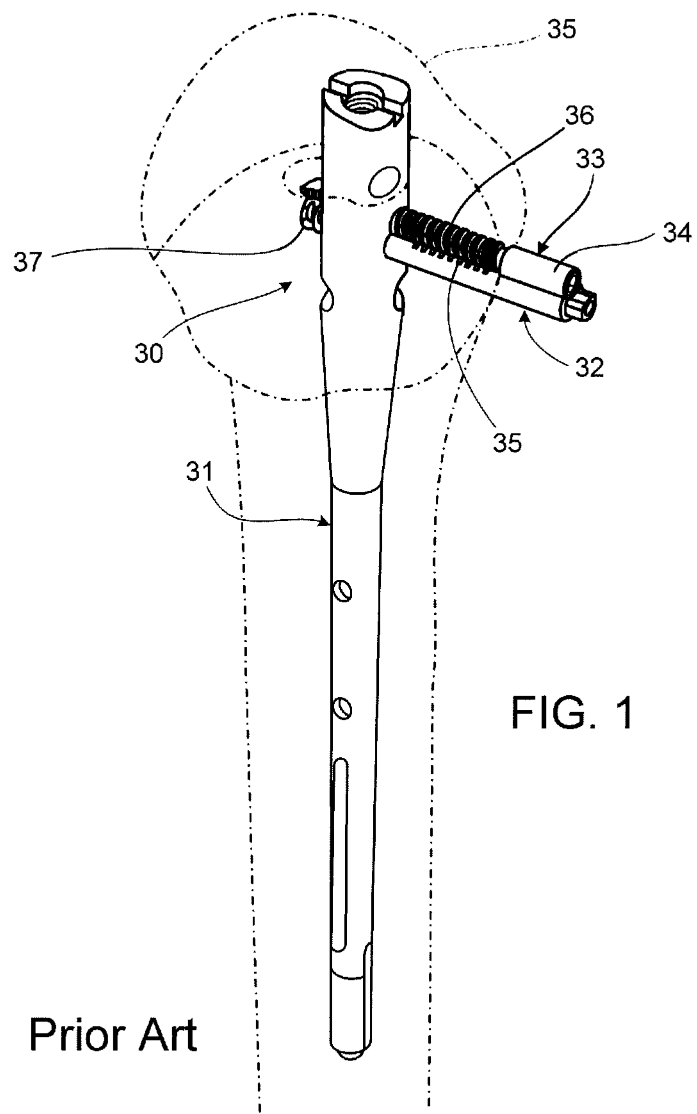
FIG. 1 is a perspective view of an intramedullary nail secured to a humerus by a fastening assembly.
Figure 2:
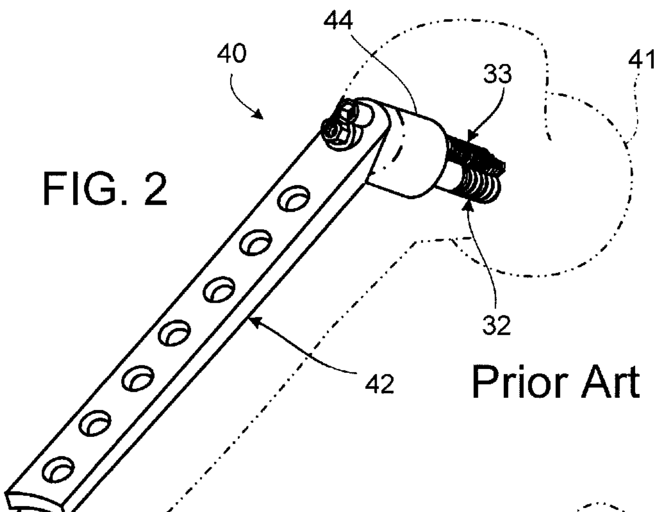
FIG. 2 is a perspective view of a fixation plate secured to a femur by a fastening assembly.
Figure 3:
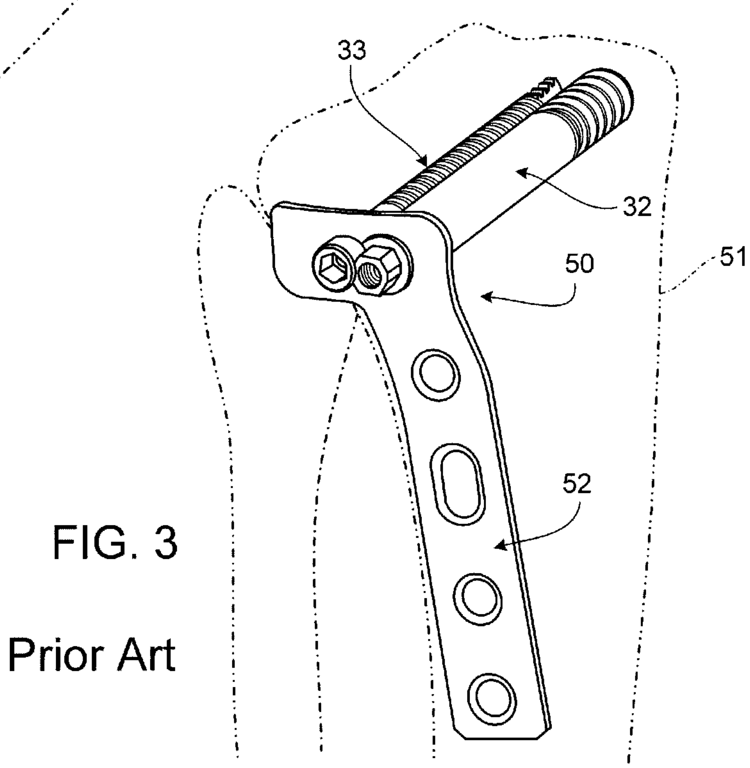
FIG. 3 is a perspective view of a fixation plate secured to a tibia by a fastening assembly.
Figure 4:
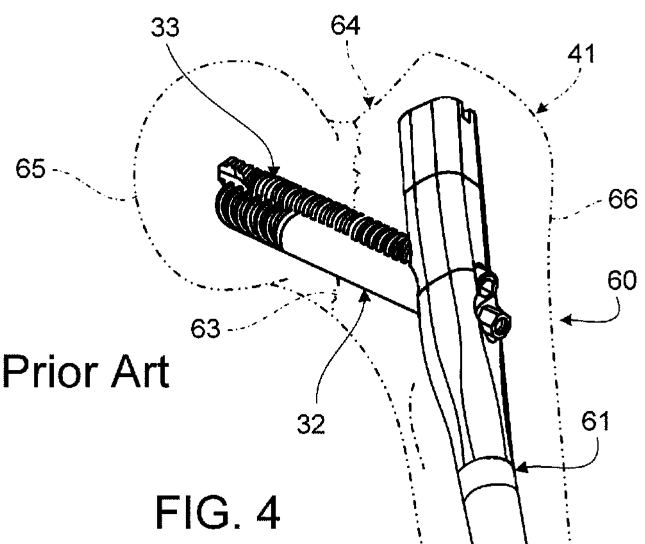
FIG. 4 illustrates a fracture across a femoral neck and a stabilization assembly.
Figure 5:
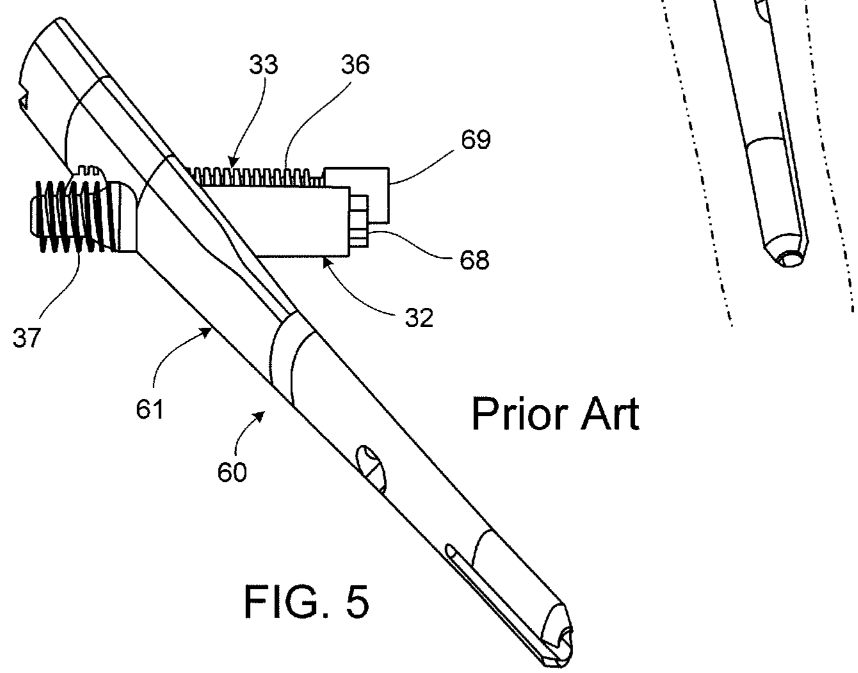
FIG. 5 is a perspective view of the stabilization assembly of FIG. 4.
Figure 6:
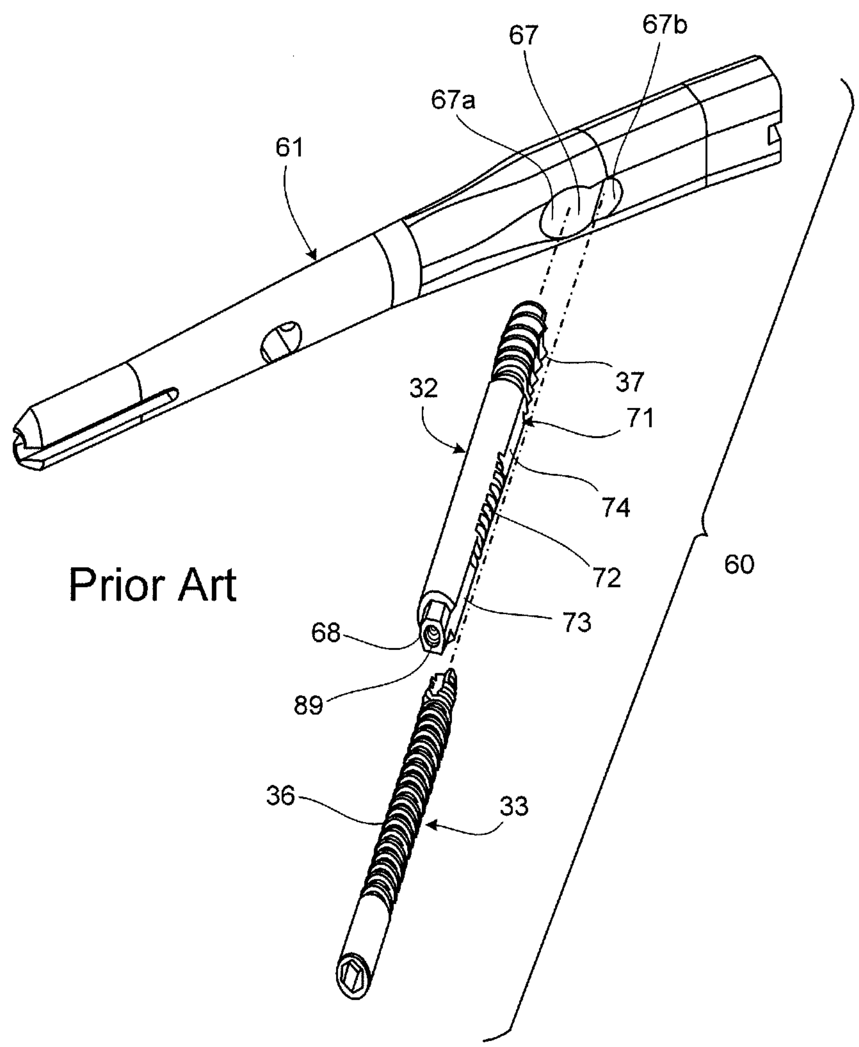
FIG. 6 is an exploded view of the stabilization assembly of FIG. 4.

Referring again to FIG. 6, the intramedullary nail 61 includes a shaped opening 67 for receiving both the lag screw 32 and the compression screw 33. During a procedure, the lag screw 32 is inserted through a corresponding larger portion **67*a* of the shaped opening 67 and rotated until the threaded distal end 37 is anchored in a desired location distal of the fracture site. The lag screw 32 is then rotated until a trough area 71, or other feature configured to engage the compression screw 33, is facing smaller portion 67*b* of the shaped opening 67 that corresponds to the compression screw 33. The proper alignment of the trough area 71 of the lag screw 32 and the compression screw 33 is illustrated in FIGS. 4-6. The compression screw 33 is then inserted through the smaller portion 67*b* of the shaped opening 67 alongside the lag screw 32. The trough area 71 of the lag screw 32 extends generally along the length of the lag screw 32 and partially accommodates the circumference of the compression screw 33 as illustrated in FIG. 7. The trough area 71 includes a middle rack 72 between otherwise smooth trough sections 73, 74 as illustrated in FIG. 8. The middle rack 72 engages the threads 36 of the compression screw 33 when the compression screw 33 is inserted through the smaller portion 67*b* of the shaped opening 67 alongside the lag screw 32. In some embodiments, the compression screw 33 and lag screw 32 may be inserted through the shaped opening 67 of the intramedullary nail 61** together.

To provide compression force on the fracture 63 and/or the bone, the compression screw 33 is rotated with the threads 36 engaged with the middle rack 72 of the lag screw 32. When the compression screw 33 engages the intramedullary nail 61, rotation of the compression screw 33 results in the lag screw 32 being pulled back out of the shaped opening 67, i.e., downward in the orientation of FIG. 6.

In FIGS. 7 and 8, the proximal end 69 of the compression screw is designed to receive a hexagonally shaped Allen-type driving tool. Of course, other types of engagements between the compression screw 33 and a compression screw driver 90 (FIGS. 12-14) could be utilized, as will be apparent to those skilled in the art. However, in FIGS. 5-8, two variations of the lag screw 32 are illustrated. In FIGS. 5 and 6, the proximal end 68 of the lag screw 32 is designed to be received in a hexagonal wrench socket, whereas in FIGS. 7 and 8, proximal end **68*a* includes a transverse slot 76 that can accommodate a blade-type driver or a forked-type driver, such as the driver 80 shown in FIGS. 9-11**.

Turning to FIGS. 9-11, a lag screw driver 80 is illustrated. In FIG. 9, an elongated cylindrical body 81 is shown attached to a handle 82. A distal end 83 of the body 81 includes a pair of prongs or forks 84 for engaging the proximal end **68*a* of the lag screw 32. The body 81 also includes proximal end 85 which is connected to the handle 82. The body 81 accommodates a retaining rod 86 (FIG. 10). The retaining rod 86 includes a proximal end 87 and a threaded distal end 88. The threaded distal end 88, which is optional, may be used to engage a threaded opening 89 in the lag screw 32, as illustrated in FIG. 6. A threaded opening may also be disposed within the slot 76 of the lag screw 32 illustrated in FIGS. 7-8. The threaded end 88 of the retaining rod 86 captures the lag screw 32 and provides assurance that the lag screw 32 will not be dropped or misplaced during a procedure. The retaining rod 86 is received within the elongated body 81 of the lag screw driver 80, as illustrated in FIG. 11. The proximal end 87 of the retaining rod 86 extends outward through the proximal end 85 of the elongated body 81. As shown below, the proximal end 87 of the rod 86 may be used as a stop against further rotation of the compression screw 33 and/or compression screw driver 90 illustrated in FIGS. 12-14. Also, the retaining rod 86 is optional, and other portions of the handle 82 or proximal end 85 of the elongated body 81 of the lag screw driver 80** may be used as the stop.

Turning to FIGS. 12-14, the compression screw driver 90 also includes an elongated body 91 with a distal end 92 and a proximal end 93. Between the distal and proximal ends 92, 93, the elongated body 91 includes a radially outwardly extending member, such as a flange 94 shown in FIGS. 12 and 14. Alternatively, other outwardly extending members may be employed as will be apparent to those skilled in the art. The elongated body 91 may be enlarged at the correct location, or may include a collar, retaining ring, clip or another structure to engage the proximal end 87 of the rod 86 and/or another stop provided on the lag screw driver 80. The compression screw driver 90 may also include a retaining rod 95 also having a threaded distal end 96 and a proximal end 97. Similar to the lag screw driver 80 discussed above, the threaded distal end 96 of the retaining rod 95 may be used to threadably engage an interior threaded portion of the compression screw 33 (not shown) to capture the compression screw and avoid the compression screw 33 being dropped or otherwise misplaced during a procedure. Like the retaining rod 86 of the lag screw driver 80, the retaining rod 95 of the compression screw driver 90 is optional. The distal end 92 of the compression screw driver 90 is hexagonally shaped to be received in the proximal end 69 of the compression screw 33, as illustrated in FIGS. 6-8. Alternatively, other coupling arrangements between the compression screw driver 90 and the compression screw 33 can be utilized, as will be apparent to those skilled in the art.

Figure 15:
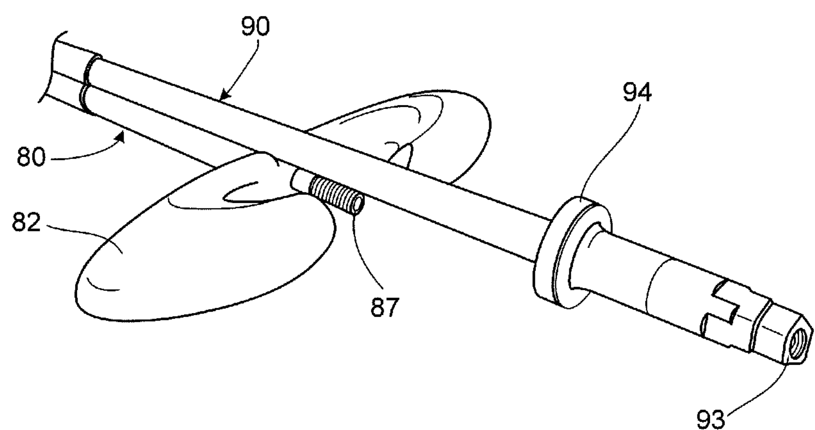
FIGS. 15-17 are perspective views of a tool set for driving fasteners.
Figure 16:
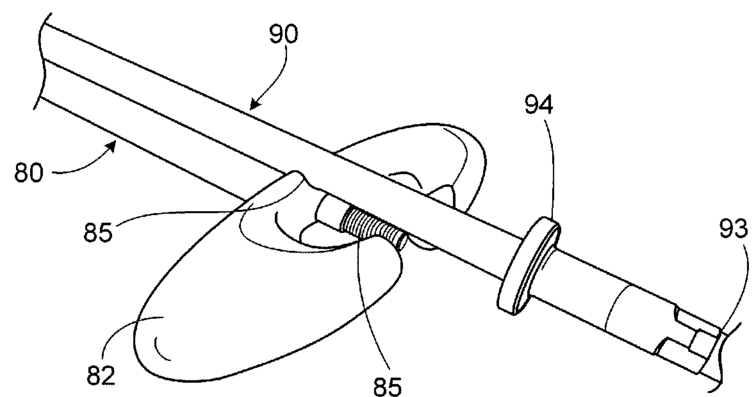
Figure 17:
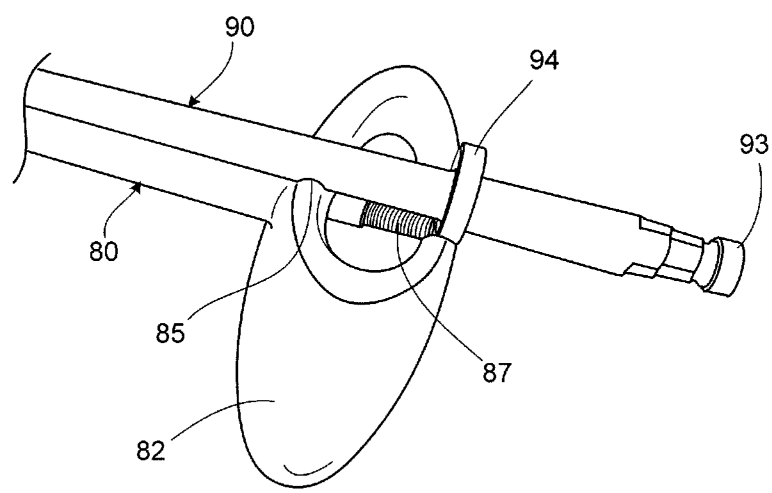

Turning to FIGS. 15-17, operation of the flange or outwardly extending member 94 and the distal end 87 of the retaining rod 86 is illustrated. In FIG. 15, the lag screw 33 has been inserted through the fixation device (not shown in FIGS. 15-17) and the handle 82 has been rotated so the threaded distal end 37 of the lag screw 32 is anchored into bone disposed distally of the fracture site (not shown in FIGS. 15-17). The compression screw driver 90 is then engaged with the proximal end 69 of the compression screw 33 (not shown in FIGS. 15-17) and, while leaving the lag screw driver 80 in place, the compression screw 33 is inserted alongside the lag screw 32 and the compression screw driver 90 engages the proximal end 69 of the compression screw 33 and is rotated. As the compression screw driver 90 is rotated while the compression screw 33 engages the intramedullary nail 61, the threads 36 of the compression screw 33 engage the middle rack 72 of the lag screw 32 and draw the lag screw 32 and the lag screw driver 80 to the right in FIGS. 15-17, i.e., towards the flange 94.

In FIG. 15, little or no compression force is exerted by the lag screw 32 on the fracture 63. In FIG. 16, the compression screw driver 90 has been rotated to an extent where at least some compression force is exerted by the lag screw 32 on the fracture 63. As seen in FIG. 16, the handle 82 has moved from the position in FIG. 15 towards the flange 94. At the point reached in FIG. 17, the handle 82 and/or the distal end 87 of the retaining rod 86 of the lag screw driver 80 engage(s) the flange 94 of the compression screw driver 90 to prevent any further rotation of the compression screw driver 90 such that no additional movement of the lag screw 32 relative to the compression screw 33 is possible. Thus, in the position shown in FIG. 17, a complete stop is achieved and, with the dimensions properly designed, over-compression of the fracture 63 by the lag screw 32 is prevented.

As mentioned above, the stop may be provided by the distal end 87 of the retaining rod 86, by the handle 82, and/or by the proximal end 85 of the elongated body 81 of the lag screw driver. Any area on the lag screw driver 80 may be employed as a stop to further rotation of the compression screw 33.

Figure 18:
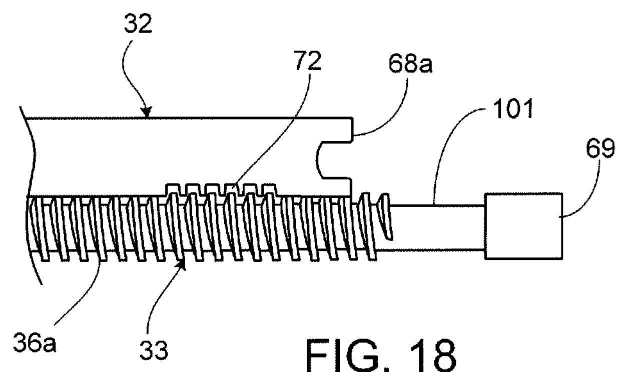
FIGS. 18-20 are side views of another fastening assembly.
Figure 19:
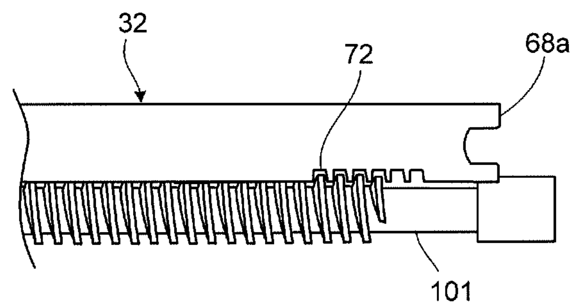

Turning to FIG. 18, the lag screw 32 is shown adjacent to a compression screw 33. The compression screw 33 includes a proximal end 69, a first threaded portion **36*a* and a second unthreaded portion 101. The lag screw 32, similar to the one illustrated in FIGS. 7 and 8, includes an elongated body and trough 71 (FIG. 8) with a distinct middle rack 72. To provide a complete stop against further movement of the lag screw 32 to the right in the orientation of FIGS. 18-19 due to rotation of the compression screw 33, the first threaded portion 36*a* of the compression screw 33 ends at the second unthreaded portion 101. As seen in FIG. 19, when the compression screw 33 has been rotated, the rack 72 of the lag screw 32 has moved to the right relative to the compression screw 33 and partially into or over the unthreaded portion 101. In the position shown in FIG. 20, the trailing edge of the middle rack 72 has reached the end of the first threaded portion 36*a* of the compression screw 33. Therefore, further rotation of the compression screw 33 will not result in any additional lateral movement of the lag screw 32 to the right because the threaded portion 36*a* disengages the rack 72**, and a complete stop is obtained.

Figure 20:
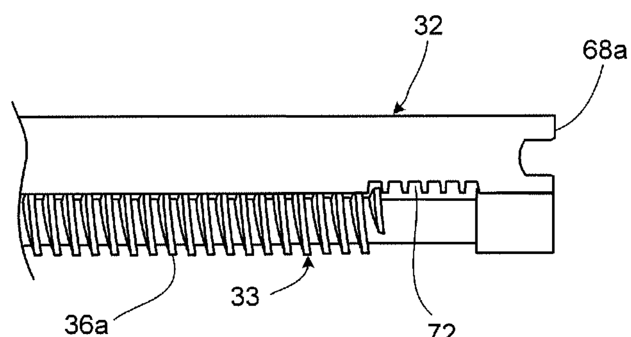

Additionally, the proximal end 69 of the compression screw 33 can be configured to engage the rack 72 to limit further advancement of the compression screw 33 relative to the lag screw 32. For example, when the compression screw 33 and the lag screw 32 are positioned as shown in FIG. 20, rotation of the compression screw will no longer cause further compression because the threaded portion **36*a* disengages from the rack 72 as described above. However, other forces may cause the compression screw 33 to advance further (or cause the lag screw 32 to retract relative to the compression screw 33), which could cause further compression. To limit further compression, the proximal end 69 can abut the rack 72 to provide a positive stop that prevents the compression screw 33 from moving relative to the lag screw 32** causing further compression.

While selected implementations have been set forth, alternatives and modifications will be apparent from the above description to those skilled in the art that fall within the spirit and scope of this disclosure and the appended claims.

The invention claimed is:

1. A system for limiting the compression force applied by an orthopaedic fastening assembly, the system comprising:

a first component driver comprising (i) a distal end configured to engage a first fastener of the fastening assembly and (ii) a proximal end including a stop, wherein the distal end of the first component driver comprises a first element for rotating the first fastener, wherein the first element is selected from the group consisting of a female polygonal wrench socket, a male polygonal wrench, a transverse driver blade, an Allen-type driver element, a Phillips-type driver element, and a pair of prong members; and a second component driver comprising (i) a distal end configured to engage a second fastener of the fastening assembly while the second fastener is arranged side-by-side with the first fastener, (ii) a proximal end, and (iii) a shaft extending between the proximal end and the distal end, the distal end of the second component driver comprising a second element for rotating the second fastener, wherein the second element is selected from the group consisting of a female polygonal wrench socket, a male polygonal wrench, a transverse driver blade, an Allen-type driver element, a Phillips-type driver element, and a pair of prong members, wherein the second component driver includes a structure that extends outwardly from the shaft of the second component driver and extends around the shaft, wherein the structure is disposed between the proximal end and the distal end of the second component driver, and wherein the structure has a distal-facing surface that is configured to engage the stop of the first component driver to limit axial translation of the first fastener relative to the second fastener.

2. The system of claim 1, wherein the proximal end of the first component driver comprises a handle, and the stop is included on the handle.

3. The system of claim 1, wherein the first component driver further comprises an elongated cylindrical body extending between the proximal end and the distal end of the first component driver, and a retaining rod disposed within the elongated cylindrical body, the retaining rod comprising a proximal end that extends outward from the cylindrical body and serves as the stop.

4. The system of claim 1, wherein the shaft of the second component driver comprises an elongated cylindrical body extending between the proximal end and the distal end of the second component driver, the second component driver further comprising a retaining rod disposed within the elongated cylindrical body and including a threaded distal end that threadably engages the second fastener.

5. The system of claim 1, wherein the stop of the first component driver is fixed to the first component driver, and wherein the structure of the second component driver is fixed to the second component driver.

6. The system of claim 1, wherein the structure is attached to the shaft of the second component driver such that, before engagement of the distal-facing surface of the structure with the stop, the structure moves relative to the stop as the second component driver moves the second fastener relative to the first fastener.

7. The system of claim 1, wherein the distal-facing surface of the structure is configured to engage the stop such that engagement of the distal-facing surface of the structure with the stop limits rotation of the second component driver or the second fastener.

8. The system of claim 1, wherein the first fastener is a lag screw, and the second fastener is a compression screw.

9. The system of claim 1, wherein the structure comprises a flange that extends outwardly from the shaft of the second component driver and extends around the shaft, and wherein the flange comprises the distal-facing surface of the structure.

10. The system of claim 1, wherein the structure comprises one of a collar, ring, clip, or flange that extends circumferentially around the shaft.

11. The system of claim 1, wherein the shaft of the second component driver has a longitudinal axis, and wherein the shaft of the second component driver extends proximally beyond the structure along the longitudinal axis.

12. A system for limiting the compression imposed by an orthopedic implant assembly, the system comprising:

a first fastener assembly member comprising a threaded distal end, a proximal end, and an elongated body extending therebetween, the elongated body of the first fastener assembly member having a cooperation structure having a predetermined axial length and not extending to the distal end or the proximal end of the first fastener assembly member; and a second fastener assembly member comprising a distal end, a proximal end, and an elongated body extending therebetween, the elongated body of the second fastener assembly member having a first portion and a second portion, the first portion being disposed between the proximal end and the distal end of the second fastener assembly member, and the second portion being disposed between the proximal end of the second fastener assembly member and the first portion, the first portion having a complimentary cooperation structure configured to engage the cooperation structure of the first fastener assembly member, and the second portion being configured to not engage the cooperation structure of the first fastener assembly member, wherein, when the second fastener assembly member is located adjacent to the first fastener assembly member so that the complimentary cooperation structure of the first portion of the second fastener assembly member is engaged with the cooperation structure of the first fastener assembly member, rotation of the second fastener assembly member results in axial movement of the first fastener assembly member relative to the second fastener assembly member until the complementary cooperation structure disengages from the cooperation structure to stop the axial movement resulting from the rotation before the cooperation structure of the first fastener assembly member reaches the proximal end of the second fastener assembly member.

13. The system of claim 12 wherein portions of the elongated body of the first fastener assembly member disposed between the cooperation structure of the first fastener assembly member and the proximal end of the first fastener assembly member are configured to not engage the complimentary cooperation structure of the second fastener assembly member, and wherein portions of the elongated body of the first fastener assembly member disposed between the cooperation structure of the first fastener assembly member and the distal end of the first fastener assembly member are configured to not engage the complimentary cooperation structure of the second fastener assembly member.

14. The system of claim 12 wherein the cooperation structure of the first fastener assembly member is disposed within a trough of the elongated body of the first fastener assembly member.

15. The system of claim 12, wherein the second portion of the second fastener assembly has an axial length that is at least half the axial length of the cooperation structure of the first fastener assembly.

16. The system of claim 12, wherein the second portion of the second fastener assembly has an axial length that is approximately the same length as the cooperation structure of the first fastener assembly.

17. The system of claim 12, wherein the second portion of the second fastener assembly has an axial length that is at least as long as an axial length of a head of the second fastener.

18. A system comprising:

a stabilization structure selected from the group consisting of a plate and an intramedullary nail, the stabilization structure comprising a shaped opening configured to receive a first fastener and a second fastener in a side-by-side arrangement;

a first driver having (i) a distal end configured to engage the first fastener and (ii) a proximal end having a stop surface, wherein the distal end of the first driver comprises an element for rotating the first fastener that is selected from the group consisting of a female polygonal wrench socket, a male polygonal wrench, a transverse driver blade, an Allen-type driver element, a Phillips-type driver element, and a pair of prong members; and a second driver having (i) a distal end configured to engage the second fastener and (ii) a proximal end, the distal end of the second driver comprising an element for rotating the second fastener that is selected from the group consisting of a female polygonal wrench socket, a male polygonal wrench, a transverse driver blade, an Allen-type driver element, a Phillips-type driver element, and a pair of prong members, and the second driver having a radially outwardly extending portion disposed between the proximal and distal ends thereof, the radially outwardly extending portion being configured to engage the stop surface of the first driver during use to limit relative movement between the first driver and the second driver.

19. The system of claim 18 wherein the proximal end of the first driver comprises a handle, and the stop is located on the handle.

20. The system of claim 18 wherein the first driver further comprises an elongated cylindrical body extending between the proximal and distal ends thereof, the first driver further comprising a retaining rod disposed within the elongated cylindrical body, the retaining rod comprising a proximal end that extends outward from the cylindrical body and serves as the stop.

21. The system of claim 20, wherein the retaining rod of the first driver further comprises a threaded distal end for engaging the first fastener.

22. The system of claim 21, wherein the distal end of the retaining rod of the first driver is threaded for threadably engaging the first fastener.

23. The system of claim 18 wherein the distal end of the first driver is forked for engaging and rotating the first fastener.

24. An orthopaedic device comprising:

a stabilization structure selected from the group consisting of a plate and an intramedullary nail, the stabilization structure having a shaped opening configured to receive a first member and a second member in a side-by-side arrangement;

the first member comprising a threaded distal end, a proximal end, and an elongated body extending therebetween that includes a cooperation structure, the cooperation structure having a predetermined axial length and not extending to either the distal or proximal ends of the first member; and the second member comprising a distal end, a proximal end, and an elongated body extending therebetween that includes a first portion and a second portion, the first portion being disposed between the proximal end and the distal end of the second member and the second portion being disposed between the proximal end of the second member and the first portion, the first portion having threads for engagement with the cooperation structure of the first member and the second portion being unthreaded, wherein when the second member is located adjacent to the first member so that the threads of the first portion of the second member engage the cooperation structure of the first member, rotation of the second member results in axial movement of the first member relative to the second member until the complementary cooperation structure disengages from the cooperation structure to stop the axial movement resulting from the rotation before the cooperation structure of the first fastener assembly member reaches the proximal end of the second fastener assembly member.

25. The device of claim 24 wherein portions of the elongated body of the first member disposed between the cooperation structure and the proximal end of the first member are configured to not engage the threads of the second member, and wherein portions of the elongated body of the first member disposed between the cooperation structure and the threaded distal end of the first member are configured to not engage the threads of the second member.

26. The device of claim 24 wherein the cooperation structure is disposed within a trough of the elongated body of the first member.

27. A system for limiting the compression force applied by an orthopaedic fastening assembly, the system comprising:

a first component driver comprising (i) a distal end configured to rotate a first member of the fastening assembly, (ii) a proximal end including a stop, (iii) an elongated cylindrical body extending between the proximal end and the distal end of the first component driver, and (iv) a retaining rod disposed within the elongated cylindrical body, the retaining rod comprising a proximal end that extends outward from the cylindrical body and serves as the stop; and a second component driver comprising (i) a distal end configured to rotate a second member of the fastening assembly while the second fastener is arranged side-by-side with the first fastener and (ii) a proximal end, the second component driver including a structure disposed between the proximal end and the distal end of the second component driver that is configured to engage the stop of the first component driver to limit axial translation of the first member relative to the second member.

28. A system comprising:

a stabilization structure selected from the group consisting of a plate and an intramedullary nail, the stabilization structure comprising a shaped opening configured to receive a first member and a second member in a side-by-side arrangement;

a first driver having (i) a distal end configured to rotate the first member and (ii) a proximal end having a stop surface, wherein the first driver comprises a retaining rod that is threaded for threadably engaging the first member; and a second driver having (i) a distal end configured to rotate the second member and (ii) a proximal end, the second driver having a radially outwardly extending portion disposed between the proximal and distal ends thereof, the radially outwardly extending portion being configured to engage the stop surface of the first driver during use to limit relative movement between the first driver and the second driver.

* * * * *